(12) United States Patent
Freer et al.

(10) Patent No.: US 10,451,576 B2
(45) Date of Patent: Oct. 22, 2019

(54) GROUND IMPEDANCE MEASUREMENT OF A CONDUIT SYSTEM

(71) Applicant: Eaton Intelligent Power Limited, Dublin (IE)

(72) Inventors: Benjamin Avery Freer, Syracuse, NY (US); Joseph Michael Manahan, Manlius, NY (US)

(73) Assignee: Eaton Intelligent Power Limited (IE)

( * ) Notice: Subject to any disclaimer, the term of this patent is extended or adjusted under 35 U.S.C. 154(b) by 0 days.

(21) Appl. No.: 15/483,680

(22) Filed: Apr. 10, 2017

(65) Prior Publication Data

US 2018/0299396 A1 Oct. 18, 2018

Related U.S. Application Data

(60) Provisional application No. 62/320,678, filed on Apr. 11, 2016.

(51) Int. Cl.
| | | |
|---|---|---|
| *G01N 27/20* | (2006.01) | |
| *G01R 27/18* | (2006.01) | |
| *G01N 17/04* | (2006.01) | |
| *G08B 21/18* | (2006.01) | |
| *G01N 17/02* | (2006.01) | |

(52) U.S. Cl.
CPC ............. *G01N 27/20* (2013.01); *G01N 17/04* (2013.01); *G01R 27/18* (2013.01); *G08B 21/182* (2013.01); *G08B 21/185* (2013.01); *G01N 17/02* (2013.01)

(58) Field of Classification Search
CPC ................................ G01N 27/20; G01N 17/04
See application file for complete search history.

(56) References Cited

U.S. PATENT DOCUMENTS

| | | |
|---|---|---|
| 4,471,294 A | 9/1984 | Nielsen |
| 4,884,034 A | 11/1989 | Guzman |
| 5,708,195 A | 1/1998 | Kurisu et al. |
| 5,721,019 A | 2/1998 | Ashcraft et al. |
| 5,885,911 A | 3/1999 | Ashcraft et al. |
| 6,265,880 B1 | 7/2001 | Born et al. |
| 6,552,885 B1 | 4/2003 | Campbell et al. |
| 6,843,137 B2 | 1/2005 | Keech |

(Continued)

FOREIGN PATENT DOCUMENTS

| | | |
|---|---|---|
| CN | 201724978 U | 1/2011 |
| KR | 10-1459623 B1 | 11/2014 |

(Continued)

OTHER PUBLICATIONS

International Search Report and Written Opinion for Application No. PCT/US2017/026843 dated Jul. 3, 2017.

*Primary Examiner* — Jermele M Hollington
*Assistant Examiner* — Feba Pothen
(74) *Attorney, Agent, or Firm* — Merchant & Gould P.C.

(57) ABSTRACT

A system to determine the ground impedance of a conduit system includes a conductive sheath and a resistor of known value. The conductive sheath is configured to surround a portion of a conductor housed within a conduit system. Capacitive coupling occurs between the sheath and the conductor to establish a voltage source. The resistor is electrically coupled between the voltage source and a metal component of the conduit system, and a voltage drop is read across the resistor to determine the health of the ground impedance of the conduit system.

18 Claims, 5 Drawing Sheets

(56) References Cited

U.S. PATENT DOCUMENTS

| | | |
|---|---|---|
| 7,068,040 B2 | 6/2006 | Stitt |
| 7,323,880 B2 | 1/2008 | Stitt |
| 7,965,085 B2 | 6/2011 | Blakely |
| 8,058,879 B1 | 11/2011 | Atherton |
| 8,220,484 B2 | 7/2012 | Howitt |
| 8,503,137 B2 | 8/2013 | Panetta |
| 2001/0030054 A1 | 10/2001 | Goett et al. |
| 2002/0050930 A1 | 5/2002 | Thomeer et al. |
| 2003/0226751 A1* | 12/2003 | Kasten ............... C01B 13/11 204/176 |
| 2005/0007121 A1 | 1/2005 | Burnett et al. |
| 2005/0275397 A1* | 12/2005 | Lightbody ......... G01R 15/142 324/126 |
| 2009/0212965 A1 | 8/2009 | Becattini et al. |
| 2010/0213955 A1 | 8/2010 | Herraez et al. |
| 2010/0271039 A1* | 10/2010 | Durston ............. G01R 29/26 324/533 |
| 2011/0058300 A1 | 3/2011 | Krauss et al. |
| 2011/0241891 A1 | 10/2011 | Tong |
| 2012/0038376 A1 | 2/2012 | Shukla et al. |
| 2012/0150460 A1 | 6/2012 | Balcerek et al. |
| 2012/0319660 A1* | 12/2012 | Hagenmaier, Jr. ... G01R 27/025 320/162 |
| 2013/0333474 A1 | 12/2013 | Godfrey et al. |
| 2014/0084687 A1 | 3/2014 | Dent |
| 2014/0091809 A1 | 4/2014 | Sargand et al. |
| 2015/0204775 A1 | 7/2015 | Shukla et al. |
| 2016/0306001 A1 | 10/2016 | Taylor et al. |

FOREIGN PATENT DOCUMENTS

| | | |
|---|---|---|
| RU | 112 525 U1 | 1/2012 |
| WO | 98/35237 A2 | 8/1998 |
| WO | 00/59715 A1 | 10/2000 |
| WO | 2007/128995 A1 | 11/2007 |
| WO | 2010/126933 A1 | 11/2010 |
| WO | 2014/088562 A1 | 6/2014 |

* cited by examiner

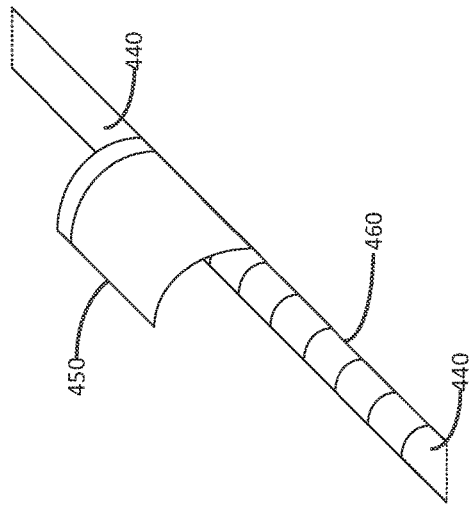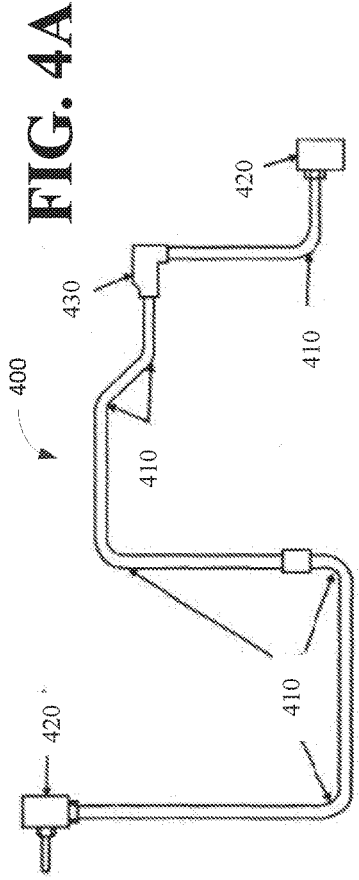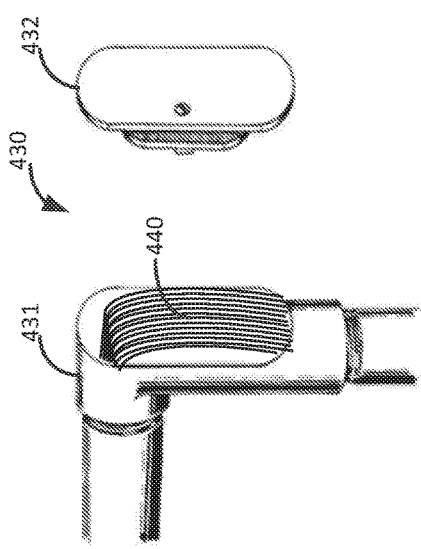

GROUND IMPEDANCE MEASUREMENT OF A CONDUIT SYSTEM

RELATED APPLICATIONS

The present disclosure claims benefit from U.S. Provisional Patent Application No. 62/320,678 filed on Apr. 11, 2016; the disclosure of which is incorporated herein in its entirety.

FIELD OF DISCLOSURE

The present disclosure generally relates to electrical grounding and, more particularly to measuring the ground impedance of a conduit system.

BACKGROUND

Grounding is an essential element of industrial electrical installations. Equipment is grounded not only to protect people that come into contact with the equipment but also to keep equipment from being harmed by fault currents, lightning strikes, the build-up of static electricity as well as electromagnetic interference and radio frequency interference. A grounding system can be as simple as ground wire tied to a single ground electrode driven into the ground or as complex as a ground grid network.

To determine that a good ground has been established and is maintained for an electrical installation, it is necessary to measure the impedance of the electrical system relative to earth ground. There are various methods to measure impedance including the traditional Fall of Potential method, which makes use of ground stakes, and the stakeless method, which makes use of a clamp on ground tester. Regardless of the method used, the measurement of a low ground impedance indicates a strongly grounded system. However, the value of the impedance that actually defines a low ground impedance has yet to be standardized. Various authorities have indicated that the system to ground impedance should be less than 5 Ohms while others have indicated that a system to ground impedance of less than 25 Ohms is acceptable.

Notably, the impedance to ground measurement methods noted above are performed with reference to an entire electrical system relative to ground. These methods do not provide the ability to test specific elements of the electrical system relative to earth ground, yet, such ability may be useful. For example, the ability to measure the ground impedance of a conduit system may be a desirable operational and safety precaution. Industrial electrical installations utilize conduit systems (e.g., various metal components including but not limited to metal conduits, fittings, housings, etc.) to protect underlying electrical wiring and electronics from exposure to detrimental environmental conditions. Because the conduit systems are made from metallic materials, their ability to conduct electricity themselves is of concern. Accordingly, care is taken to not only ground the circuits within the conduit system but to additionally ground the conduit systems themselves to help prevent the possibility of electrical shock and equipment malfunction.

SUMMARY

The present disclosure is directed to a system and method for measuring the impedance of a conduit system relative to earth ground. The ability to take this measurement provides tangible insight into the integrity of the conduit system itself, and helps to eliminate reliance on visual inspection of the conduit and/or ground impedance measurements of an entire electrical system to determine the existence of a strong ground connection.

One aspect of the present disclosure is directed to a system to determine the ground impedance of a conduit system. The system includes a conductive sheath and a resistor of known value. The conductive sheath is configured to surround a portion of a conductor housed within a conduit system. Capacitive coupling occurs between the sheath and the conductor to establish a voltage source. The resistor is electrically coupled between the voltage source and a metal component of the conduit system. A voltage across the resistor is representative of the ground impedance of the conduit system.

Another aspect of the present disclosure is directed to a method for determining the ground impedance of a conduit system. The method comprises the steps of: (1) accessing a conductor housed within a conduit system; (2) sheathing the conductor such that capacitive coupling occurs between the sheathing and the conductor with capacitive coupling operating to establish a voltage source; (3) coupling a resistor of known value between the voltage source and a metal component of the conduit system; and (4) measuring at least one of an impedance, current or voltage relative to the resistor to determine a voltage across the resistor, wherein the voltage is representative of a ground impedance of the conduit system.

The above summary is not intended to describe each embodiment or every implementation. A more complete understanding will become apparent and appreciated by referring to the following detailed description and claims in conjunction with the accompanying drawings.

BRIEF DESCRIPTION OF THE DRAWINGS

FIGS. 4A-4C are schematics illustrating a conduit system incorporating the system and method for measuring the ground impedance of a conduit system according to various embodiments of the disclosure.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
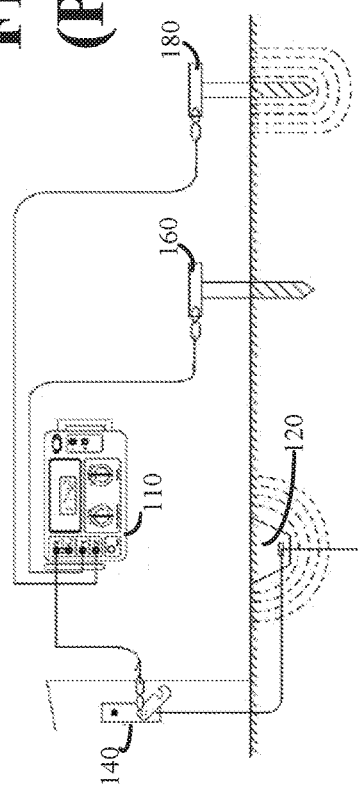
FIG. 1 is an example configuration of a system for measuring ground impedance in an electrical system.

In industrial applications, all electrical installations are required to be tied to earth ground. The electrical installations include conduit systems (metal components such as metal conduits, fittings, housings, etc.) that are provided to protect the underlying wiring and electronics. The various components of the conduit system are typically made of coated steel, stainless steel, galvanized steel, cast iron, or aluminum, some or all of which may additionally be covered in a polyvinylchloride (PVC) coating. In addition to grounding the wired circuits in the installation, the conduit system is also grounded to help prevent risk of electrical shock and damage to equipment.

The grounding of the conduit system is typically performed by tying a screw or lug (e.g., "ground screw") that is coupled to a component of the conduit system to ground. Each and every component of the conduit system is not individually tied to ground, rather direct grounding occurs only at various locations throughout the installation. This direct grounding is carried through to the other components of the conduit system via various means. For example, the metal conduits, fittings and housings of the conduit system are connected with interfacing metal threads; the metal-to-metal contact between the threads serves to transfer the grounding from component to component.

However, over time, the electrical installation may be exposed to water or corrosive chemicals causing degradation of the conduit system. For example, the threading between conduits and fittings may degrade to the point of electrical failure, and cannot be easily observed, especially if covered with PVC or another insulative coating. Thus, if a piece of conduit or an enclosure were to lose a ground connection, the loss may go unnoticed indefinitely. Accordingly, the present disclosure is directed to a system and method for determining the ground impedance of a conduit system.

Maintaining proper grounding in a system can be important both for electrical safety, as well as material safety. A system that is improperly grounded may produce stray voltages that disrupt other systems, or shock persons nearby, and cause an electrical hazard. The conditions that lead to poor grounding may cause material hazards as well before the system fails electrically. For example, a conduit that corrodes may mechanically fail and damage nearby equipment, break wiring (creating an additional electrical hazard or outage), or hurt nearby persons. Additionally, materials held within a corroding component that is improperly grounded may react with the corroded component, such as, for example, food and items stored in a corroding tank, liquids carried by corroding pipes, or industrial chemicals held within a corroding reacting vessel. Moreover, corroding electrical conduits may run above persons, equipment, or materials being processed (including food) in a facility, and may drip or drop debris from corrosion on objects below if left unmonitored. Therefore the changes in impendence indicative of a failing ground fault state may be important to learn of even before the system ground faults.

As noted in the "Background," there are a variety of methods for measuring ground impedance with respect to an entire electrical system. Most methods operate by measuring the current flow directly between two or more different ground points. See, for example, FIG. 1, which illustrates a system 100 for the selective measurement of ground impedance. This system 100 uses a specialized tester 110, which is tied to an earth ground electrode 120 (via a ground strip 140), an inner electrode 160 and an outer electrode 180. This method, which is very similar to the Fall-of-Potential method, generally places inner electrode 160 and outer electrode 180 into the ground in a direct line from the earth ground electrode 120 at a spacing of approximately sixty-five feet (roughly twenty meters). The specialized tester 110 is then connected to the earth ground electrode 120 as well as to the inner electrode 160 and outer electrode 180. The specialized tester 110 is then used to generate a current of a known value between the outer electrode 180 and the earth ground electrode 120 while the drop in voltage (V) is measured between the inner electrode 160 and the earth ground electrode 120. The current (I) flowing through the earth ground electrode 120 is also measured. The value of the voltage drop and the value of the current can then be used to calculate the ground impedance (R) by the equation V=IR.

Figure 2:
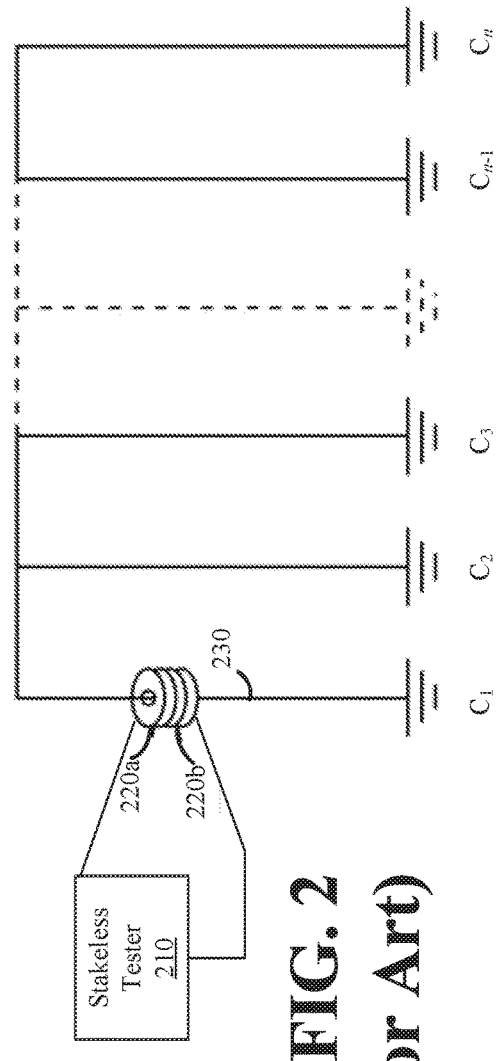
FIG. 2 is an example of another configuration of a system for measuring ground impedance in an electrical system.

A more recently developed method for measuring ground impedance of an entire electrical system is the stakeless measurement method, a system for which is illustrated in FIG. 2. As shown, the stakeless method uses a stakeless tester 210 and two clamps 220a and 220b (collectively, clamps 220). The two clamps 220 are placed around an earth ground rod 230 (leading to selected earth ground $C_1$ of the earth ground rods $C_1$-$C_n$) and are connected to the stakeless tester 210. The concept behind this method is that the net resistance of all ground paths will be extremely low compared to the single path that is being tested, and the net resistance of all parallel return path resistances is effectively zero. A known voltage is then induced by the first clamp 220a and the current is measured with the second clamp 220b while the stakeless tester 210 automatically determines the ground loop resistance at the selected earth ground rod 230. The ground impedance of each of the earth ground rods $C_1$ through $C_n$ is measured separately, with the selected earth ground rod 230 and the clamps 220 changing for each measurement.

The solutions described above rely on the ability to access the ground carrying conductor, (i.e., earth ground electrode or earth ground rod), in order to measure a current flowing through it. However, in trying to determine the ground impedance of a conduit system, it is infeasible to measure the current flowing through one or more of the components (conduit, fitting, housing, etc.) of the conduit system. Notably, it would be difficult to induce a current in a conduit and, even if it were possible, the current in the conduit would reflect interference from the currents flowing in the wiring/conductors that the conduit is housing. Accordingly, described herein below is a system and method for measuring ground impedance in a conduit system.

Figure 3:
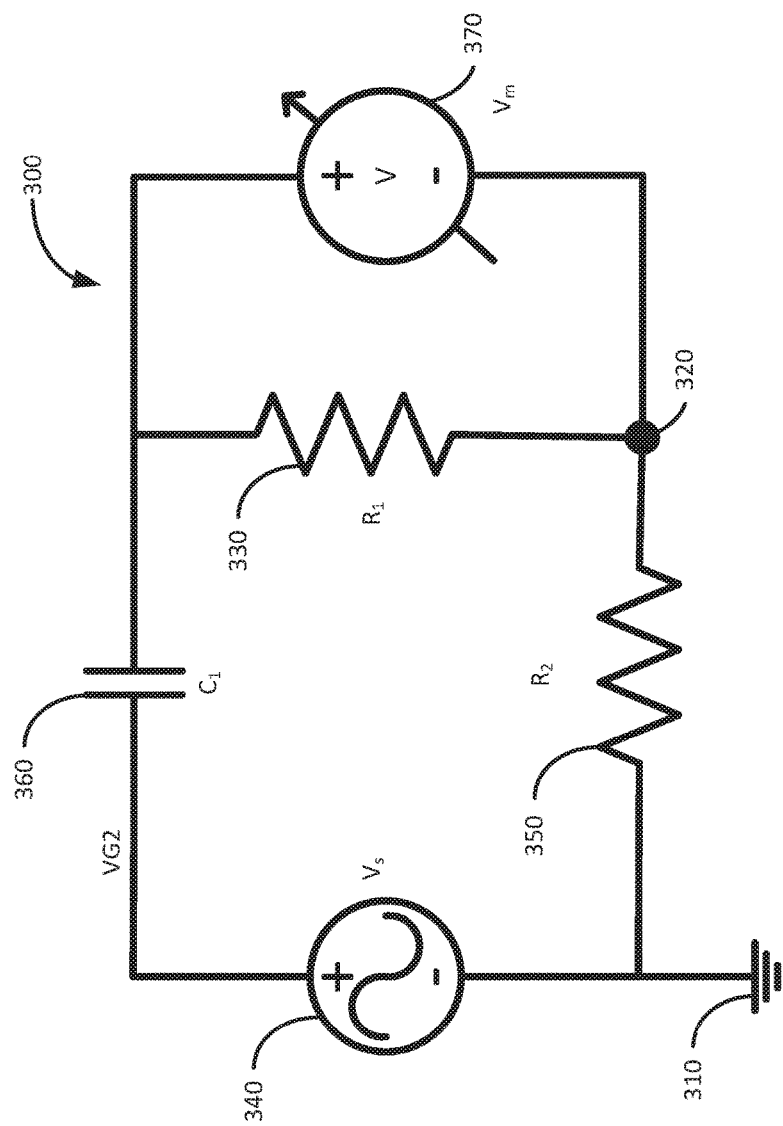
FIG. 3 is circuit representing a system for measuring the ground impedance of a conduit system according to various embodiments of the present disclosure.

The circuit 300 of FIG. 3 illustrates the ground impedance measurement system of the present disclosure. As shown, the circuit 300 includes an earth ground 310 and a common node 320, which represents a single point connection to a metal component (e.g., conduit, fitting, housing) of the conduit system being measured. The circuit 300 further includes a first resistor 330 of known resistance ($R_1$), operating as a current sense resistor, that is tied to the common node 320 as well as a high impedance voltage source 340 providing a voltage $V_s$ that is applied across a second resistor 350 of resistance $R_2$. In this configuration, the second resistor 350 of resistance $R_2$ represents the impedance of the conduit system back to the earth ground 310 from the common node 320. A capacitor 360 of capacitance $C_1$ represents capacitive coupling that controls the impedance of the high impedance voltage source 340. A measurement device 370, such as, for example, a voltmeter, is provided to measure the voltage ($V_m$) across the first resistor 330 of resistance $R_1$.

In one example embodiment, a conductive shielding fabric is used to produce the high impedance voltage source 340 via capacitive coupling with one of the live conductors housed by the conduit system. This capacitive coupling with the conductor enables the high impedance voltage source 340 to have a ground that is common with the conduit system, a feature which enables the described ground impedance measurement systems and methods to work via a closed, current loop. The conductive shielding fabric may, for example, comprise ZT-SHIELD™ available from the Zippertubing Company of Chandler, Ariz. The ZT-SHIELD™ is described as a combination of fire retardant Polyurethane ZT-TAPE®, also available from Zippertubing Co., stagger bonded to a layer of Z-3250-CN shielding fabric with an electrically conductive adhesive backing.

The voltage source established with the capacitive coupling comprises a high impedance voltage source $340$ due to the limited charge that can be transferred from the conductor to the shielding through its capacitance. In using the conductive shielding fabric, the impedance $Z_C$ of the capacitive coupling, is determined according to EQUATION 1 where in one example: w=$2\pi*60$ Hz (for a 60 Hz system) and the capacitance $C_1$ of capacitor $360$ is 100 pF:

$$Z_C = \frac{1}{wC_1} = \frac{1}{(2\pi \times 60 \times 100 \times 10^{-12})} \approx 26.5 \ M\Omega \quad \text{(EQUATION 1)}$$

The first resistor $330$ is selected at a known resistance $R_1$ value sufficient to divide the voltage down from $V_s$ to a measurable level, e.g., a level that can be measured by a low voltage voltmeter, multimeter, microcontroller or other measurement device $370$. In a 120 V electrical installation (i.e., a system with VG2=120 V), when using the conductive shielding fabric as described above, a value of 1 MΩ has been found acceptable for $R_1$, but one of ordinary skill in the art will be able to select other values of $R_1$ appropriate to the installation. If one were to presume a perfect conduit connection to ground (e.g., zero Ohm ground impedance $R_2$), an $R_1$ value of 1 MΩ and a $C_1$ value of 100 pF in a 60 Hz system, the voltage measured ($V_m$) across the first resistor $330$ in FIG. 3, could then be calculated as:

$$V_m = \frac{VG2 \times R1}{(Z_{C1} + R1)} = \frac{120 \ V \times 1M}{26.5M + 1M} \approx 4.4 \ V \text{ (ideal value)} \quad \text{(EQUATION 2)}$$

Any voltage below the ideal maximum voltage, e.g. below the 4.4 V in the above example, would indicate a weakened ground connection. For example, if a ground impedance of the conduit (represented by the second resistor $350$) is no longer zero Ohms, but sits at $R_2$=100 kΩ, the resulting measured voltage across $R_1$ would be determined as follows:

$$V_m = \frac{VG2 \times R1}{(Z_{C2} + R1 + R2)} = \frac{120 \ V \times 1M}{26.5M + 1M + 100k} = 4.35 \ V \quad \text{(EQUATION 3)}$$

At a point just before complete failure of the conduit ground connection, the impedance of the conduit system may rise up, for example, to 1 MΩ for $R_2$, resulting in a voltage across $R_1$ of 4.2 V. After complete failure of the ground connection, there is no current through $R_1$, or $R_2$, and the measured voltage ($V_m$) across $R_1$ is zero.

Further illustration of the ground impedance measurement system is provided with reference to the aspects of conduit systems shown in FIGS. 4A-4C. In FIG. 4A, a conduit system $400$ includes various metal conduit runs $410$ (straight or bent), metal outlet boxes $420$, and may include a metal CONDULET® outlet body $430$, provided by Eaton Corp. of Cleveland, Ohio. In various aspect, the metal components may be covered in PVC, insulative foam, paint, patina, galvanization, or another surface layer.

A detailed illustration of an outlet body $430$ is provided with respect to FIG. 4B. The outlet body $430$ includes a base portion $431$ and a removable cover $432$. An installer may access the conductors $440$ housed within the conduit system $400$ through an access point, for example, the outlet body $430$ or other easily accessible component.

A detailed illustration of a conductor $440$ is provided with respect to FIG. 4C. With the cover $432$ removed to expose the underlying conductors $440$, the installer may wrap a conductive shielding fabric $450$ about one or more of the conductors $440$ within the outlet body $430$. As the shielding fabric $450$ is wrapped, it adheres to itself to the conductor $440$, establishing a continuous electrically conductive sheath $460$ around the conductor $440$. Due to the amount of surface area that the sheath $460$ has in common with the conductor $440$, capacitive coupling between the sheath $460$ and conductor $440$ occurs (even if the conductor $440$ is insulated). In a 120 V electrical installation, a sheath $460$ of approximately twelve inches (thirty cm) has been found sufficient to create the capacitive coupling necessary to produce the desired voltage. As will be appreciated, higher voltage installations may use sheaths $460$ shorter in length, and lower voltage installations may use sheaths $460$ longer in length to produce the desired voltage.

With capacitive coupling established between the sheath $460$ and the conductor $440$, a known resistance, e.g., $R_1$, can be coupled between the sheath $460$ and the base portion $431$ of the outlet body $430$ (or other metal component of the conduit system $400$) thereby creating a current loop. The voltage across the known resistor $330$ can be then be measured with an appropriate measurement device $370$, e.g., voltmeter, multimeter, microprocessor, etc. Any voltage measured across the known resistor $330$ that is below the ideal maximum voltage indicates a weakened ground connection. The weakened ground connection indicates that the conduit system impedance $R_2$, from the single point (common node $320$) at which the known resistor $330$ is connected to the base portion $431$, is above zero Ohms and the conduit system $400$ has suffered some degradation. A voltage of zero Volts across the known resistor $330$ indicates a complete failure of the grounding of the conduit system $400$. As will be appreciated, because the impedance sensing current through the known resistor $330$ is generated from the line voltage of the conductor $440$, the measurement sensitivity increases with the line voltage.

The above-described ground impedance measurement system may be implemented while in the field, via a straightforward retrofit without any need to cut a conductor $440$. The installation of the ground impedance measurement system can be performed in minutes and, if performed at a CONDULET® outlet body, need only involve an outlet body cover $432$ replacement.

Figure 5:
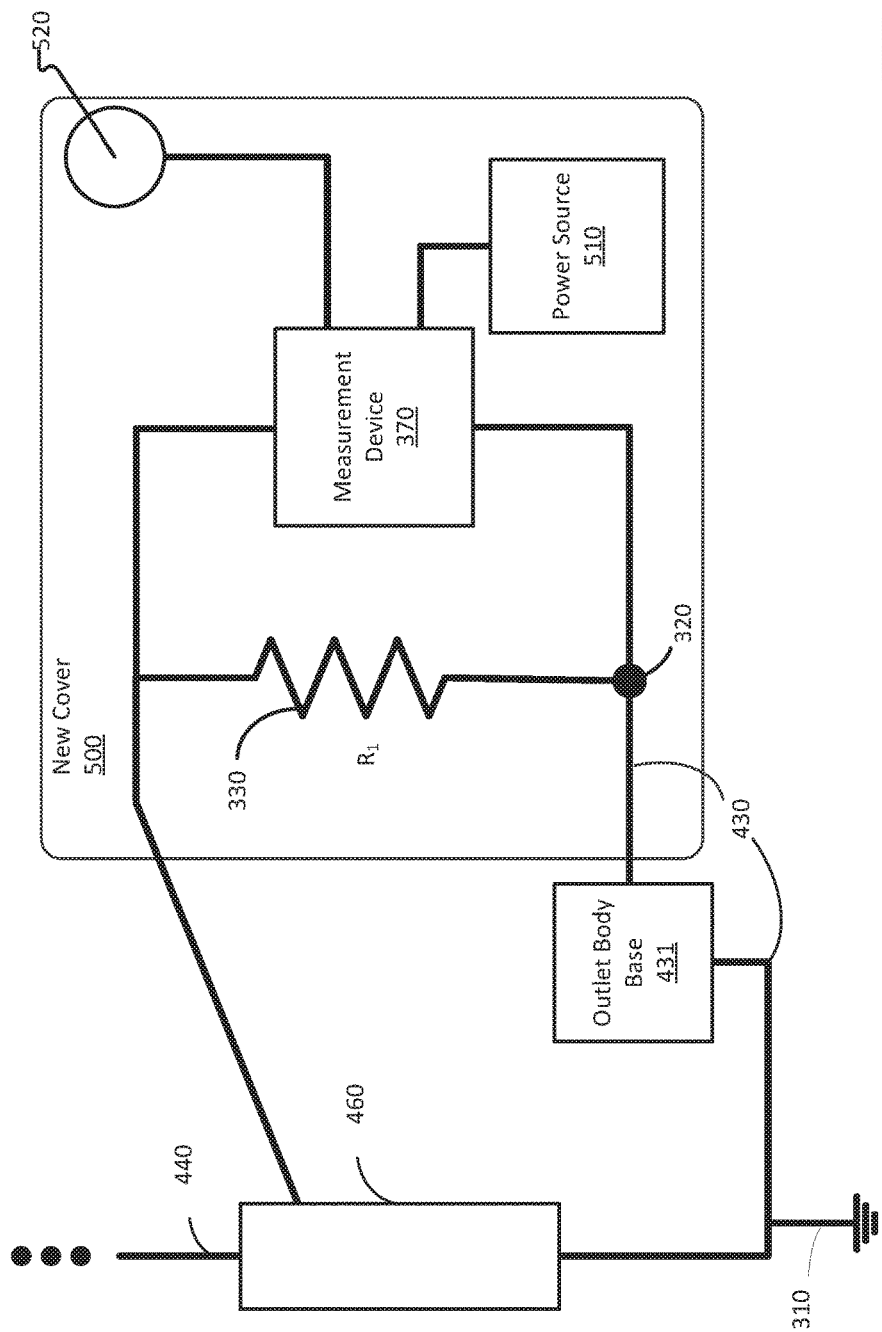
FIG. 5 is a schematic of an example embodiment of a cover of a conduit system outlet body incorporating the electronics of the ground impedance measurement system according to various embodiments of the disclosure.

FIG. 5 is a schematic of an example embodiment of a new cover $500$ of a conduit system outlet body $430$ incorporating the electronics of the ground impedance measurement system according to various embodiments of the disclosure. As illustrated in the example embodiment, the sheath $460$ is left in place about the conductor $440$ while the cover $431$ of the outlet body $430$ is fitted with, or replaced with a new cover $500$ containing, the electronics discussed herein for the continuous monitoring of the ground impedance of the conduit system $400$. The electronics incorporated into the new cover $500$ include: a first resistor $330$ of known resistance $R_1$ connected between the sheath $460$ and the base portion 431 of the outlet body 430; a measurement device 370 (e.g., a voltmeter, multimeter, microprocessor) for measuring a voltage $V_m$ across the first resistor 330; and power source 510 for powering the measurement device 370 (e.g., a battery, or an inductive coil drawing power from the conductor 440). The electronics may additionally include an indicator 520 (e.g., visual alarm or audio alarm) to alert a passer-by of a failing or failed conduit ground impedance or a wireless transmitter for transmitting an alarm signal to a monitoring system to enable real-time monitoring. Note that the common node 320 to ground 310 by the conductor 440 and the conduit system 400, via outlet body 430, creates a closed current loop.

Figure 6:
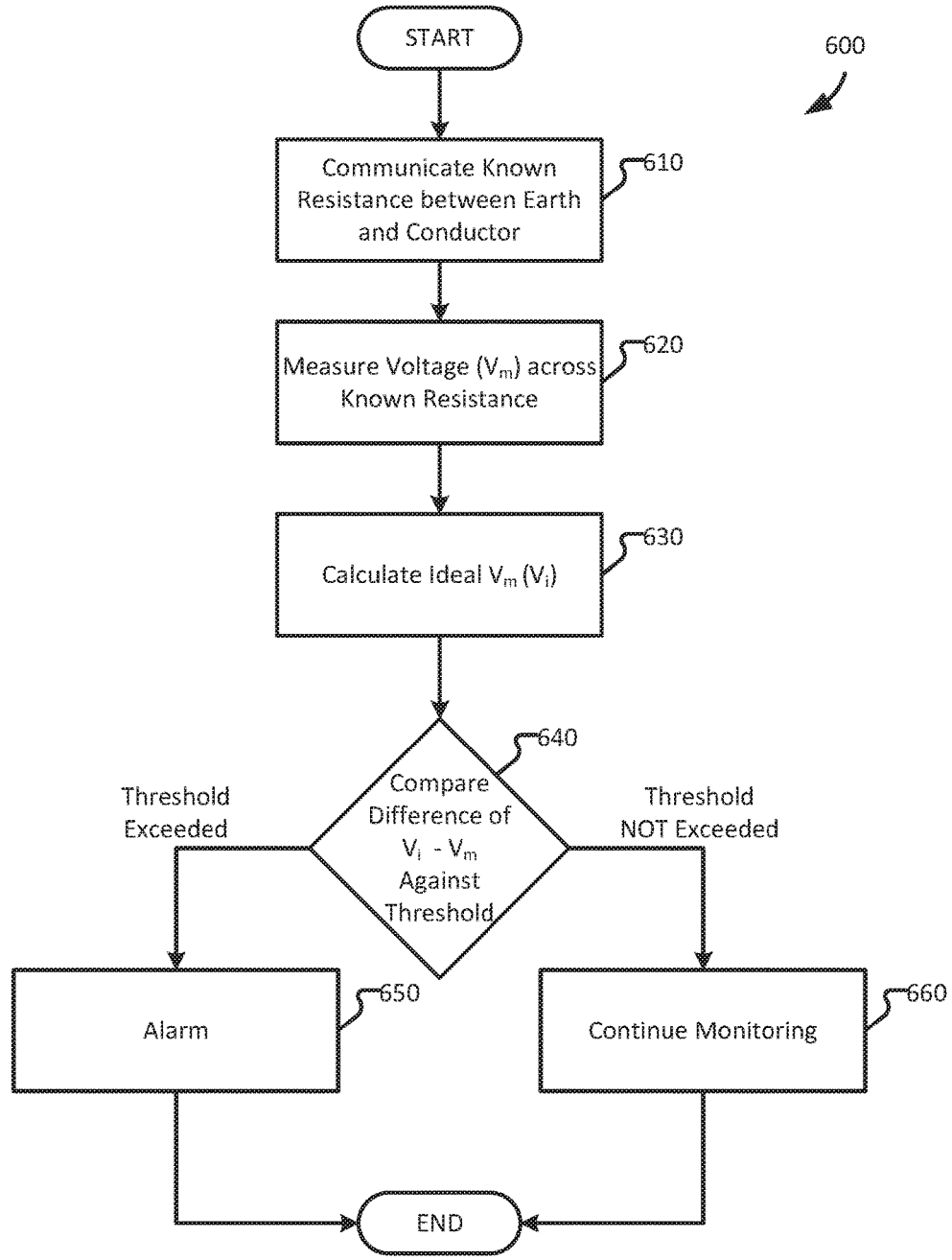
FIG. 6 is a flow chart illustrating general steps of an example method for measuring the ground impedance of a conduit system according to various embodiments of the present disclosure.

FIG. 6 is a flow chart illustrating general steps of an example method 600 for measuring the ground impedance of a conduit system according to various embodiments of the present disclosure. Method 600 begins at OPERATION 610, where a resistor 330 of known resistance (e.g., the first resistor 330 of resistance $R_1$) is communicated between earth ground 310 and a conductor 440 carrying current. The resistor 330 may be communicated to the ground by soldering the resistor 330 to an existing cover 432 or component of the conduit system, integrating it in a new cover 500 (and mounting the cover to the conduit system so that they are in electrical communication), using a ground lug, etc. In various aspects, the resistor 330 is communicated to the conductor 440 by wrapping conductive shielding fabric 450 to form a sheath 460 around the conductor 440 to capacitively couple the sheath 460 and conductor 440, with a lead running to the resistor 330, with a pre-formed capacitive sheath 460 with a lead running to the resistor 330 slid around the conductor 440, or a specially configured conductor 440 with a coaxial conductive shield that includes a lead running to the resistor 330.

Proceeding to OPERATION 620, a voltage $V_m$ is measured across the resistor 330 of known resistance. A measurement device 370, such as a voltmeter, multimeter, microcontroller, etc., measures the voltage across the resistor 330, which is compared against an ideal $V_m$ ($V_i$), that is calculated for the system measuring the ground impedance that is calculated in OPERATION 630. The value of $V_i$ is calculated as described above in relation to EQUATIONS 1 and 2. In various aspects, the value of $V_i$ may be pre-calculated at the time of manufacture of the system and stored in the measurement device 370 or an indicator 520 (or an associated microcontroller). Various controls, such as switches, dials, and sliders, may be used by an operator to vary the values used in the equations to match the system being measured. For example, an operator may changing a frequency used in EQUATION 1 between 60 Hz and 50 Hz with a switch, change a voltage used in EQUATION 2 between 110 V and 250 V with a dial, etc.

The difference between the ideal voltage $V_i$ and the measured voltage $V_m$ is compared against a voltage threshold at DECISION 640. As will be appreciated, different aspects may use different voltage thresholds to indicate grounding failure at an earlier or later state of degradation. For example, a threshold for a larger difference in voltages may be useful for applications with greater tolerance for minor corrosion, while applications with lower tolerance for corrosion (e.g., food storage, chemical reactions) may use a lower voltage threshold. A voltage threshold may be stored in a microprocessor associated with the measurement device 370 and the indicator 520, or may be set (or chosen) by an operator via various controls, such as, for example, switches, dials, or sliders.

In other aspects, EQUATION 3 is used to determine a value of the impedance of the system being measured (i.e., the value $R_2$ of the second resistor 350). The value of $R_2$ indicates the strength of the grounding for the system, with $0\Omega$ being ideal and $\infty\Omega$ (or values approaching infinite) indicating failure of the grounding. In this alternative aspect, OPERATION 630 may be omitted, and the calculated value of $R_2$ is compared against a resistance threshold at OPERATION 640. As will be appreciated, different aspects may use different resistance thresholds to indicate grounding failure at an earlier or later state of degradation. For example, a larger resistance threshold may be useful for applications with greater tolerance for minor corrosion, while applications with lower tolerance for corrosion (e.g., food storage, chemical reactions) may use a lower resistance threshold. A resistance threshold may be stored in a microprocessor associated with the measurement device 370 and the indicator 520, or may be set (or chosen) by an operator via various controls, such as, for example, switches, dials, or sliders.

When the threshold is determined to have been exceeded in DECISION 640, method 600 proceeds to OPERATION 650, where an alarm is raised. In various aspects, the alarm is raised as long as the measurements exceed the threshold and the alarm is cleared when the measurements for not exceed the threshold, while in other aspects, the alarm is raised until an operator clears the alarm state. An alarm may be communicated by the indicator 520 (e.g., a light, speaker, or radio device for transmitting the alarm state to a central monitoring system), and one of ordinary skill in the art will appreciate the benefits and drawbacks to different types of indicators 520 and whether the alarm state is maintained or automatically cleared when the conditions drop below the threshold that caused the alarm. Method 600 then concludes.

When the threshold is determined to not have been exceeded in DECISION 640, method 600 proceeds to OPERATION 660, where the monitoring system continues to measure the voltage across the first resistor 330 to monitor the health of the grounding of the conduit system. Method 600 then concludes.

Various other modifications may be made to the ground impedance measurement system, which may include variations to the capacitive coupler used instead of or in addition to the sheath 460 discussed above. For example, the wrappable tape configuration of the conductive shielding fabric described above is especially suited to retrofit applications, however, in a non-retrofit situation, e.g., a new installation, the wrappable tape may be replaced with a pre-formed, conductive sheath 460 into which the conductor 440 is slid. Such a sheath 460 may be several feet in length to provide additional capacitive coupling. Yet another aspect provides for elimination of the conductive sheath 460 in favor of a specially configured conductor 440. For example, a conductor 440 constructed with an outer conductive shield (i.e., a secondary conductor that nominally does not supply voltage or current to the load), similar to a coaxial cable construction to which the known resistor 330 may be coupled. In further examples, a clamp or donut may be used as a capacitive coupler. As will be appreciated, at various points in a conduit system, different capacitive couplers may be used.

In one aspect, the present disclosure is implemented as a system to determine the ground impedance of a conduit system comprising a capacitive coupler and a resistor of known value, wherein the capacitive coupler is configured to surround a portion of a first conductor housed within a conduit system, wherein capacitive coupling occurs between the capacitive coupler and the first conductor to establish a voltage source, and wherein the resistor is electrically coupled between the voltage source and a metal component of the conduit system, wherein a voltage across the resistor is representative of the ground impedance of the conduit system. In some aspects, a voltage across the resistor is less than an ideal voltage but greater than a zero voltage indicates a weakening ground impedance of the conduit system, such that the weakening ground impedance of the conduit system alerts to a corrosion state of the conduit system. In some aspects system of claim further comprises an indicator coupled to the resistor, the indicator configured to provide an indication of the weakening ground impedance. In additional aspects, the capacitive coupler comprises a conductive tape wrapped a plurality of times around the conductor to form a conductive sheath. In further aspects, the system further comprises a measurement device configured to measure the voltage across the resistor. In some aspects, the measurement device is powered inductively by a second conductor within the conduit system, wherein the second conductor is different from the first conductor. In yet further aspects, a clamp-on current transformer is coupled between the second conductor and the measurement device to inductively power the measurement device.

In a second aspect, the present disclosure is implemented as a method for determining ground impedance of a conduit system, the method comprising: accessing a first conductor housed within a conduit system; communicating a portion of the first conductor with a capacitive coupler such that capacitive coupling occurs between the capacitive coupler and the first conductor, the capacitive coupling operating to establish a voltage source; coupling a resistor of known value between the voltage source and a metal component of the conduit system, and measuring a voltage drop across the resistor, wherein the voltage drop is representative of the ground impedance of the conduit system. In some aspects, a voltage across the resistor is less than an ideal voltage, but greater than a zero voltage, indicates a weakening ground impedance of the conduit system. Further, in some aspects, where the voltage indicates a weakening ground impedance, the method comprises providing an indication of the weakening ground impedance of the conduit system. Further still, in some aspects of the method, the indication of the weakening ground impedance provides an alert to corrosion within the conduit system. In other aspects, the step of communicating comprises wrapping a conductive tape a plurality of times about the first conductor to form a conductive sheath as the capacitive coupler. In yet other aspects, the step of measuring is performed by a measurement device inductively powered by a second conductor housed within the conduit system, wherein the first conductor is different from the second conductor. In some aspects, a clamp-on current transformer is coupled between the second conductor and the measurement device to inductively power the measurement device. In yet further aspects, the conductor is an insulated conductor.

In a third aspect, the present disclosure is implemented as a method to determine the ground impedance of a conduit system, the method comprising—calculating an impedance of the conduit system based on: a voltage of a voltage source formed by a capacitive coupling between a first conductor and a coupler having a known impedance value, a known resistance value of a resistor in communication between the voltage source and a metal component of the conduit system, a voltage to ground value for the conduit system, and a measured voltage drop across the resistor; determining whether the impedance of the conduit system exceeds a failure threshold; and in response to determining that the impedance exceeds the failure threshold, generating a ground fault alert. In some aspects, the method further comprises in response to determining that the impedance no longer exceeds the failure threshold, clearing the ground fault alert. In other aspects, the measured voltage drop across the resistor is measured by a measurement device inductively powered by a second conductor housed within the conduit system, wherein the first conductor is different from the second conductor. In further aspects, the coupler having the known impedance value is a conductive tape wrapped a plurality of times about the first conductor to form a conductive sheath.

Systems, devices or methods disclosed herein may include one or more of the features structures, methods, or combination thereof described herein. For example, a device or method may be implemented to include one or more of the features and/or processes above. It is intended that such device or method need not include all of the features and/or processes described herein, but may be implemented to include selected features and/or processes that provide useful structures and/or functionality.

Various modifications and additions can be made to the disclosed embodiments discussed above. Accordingly, the scope of the present disclosure should not be limited by the particular embodiments described above, but should be defined only by the claims set forth below and equivalents thereof.

What is claimed is:

1. A system to determine the ground impedance of a conduit system, the system comprising:
   a capacitive coupler, wherein the capacitive coupler includes a conductive tape wrapped a plurality of times around a first conductor housed within a conduit system to form a conductive sheath, wherein capacitive coupling occurs between the conductive sheath and the first conductor to establish a voltage source; and
   a resistor of known value, the resistor electrically coupled between the capacitive coupler and a metal component of the conduit system, wherein a voltage across the resistor is representative of the ground impedance of the conduit system.

2. The system of claim 1, wherein a voltage across the resistor of less than an ideal voltage but greater than a zero voltage indicates a weakening ground impedance of the conduit system.

3. The system of claim 2, wherein the weakening ground impedance of the conduit system alerts to a corrosion state of the conduit system.

4. The system of claim 1, further comprising an indicator coupled to the resistor, the indicator configured to provide an indication of the weakening ground impedance.

5. The system of claim 1, further comprising a measurement device configured to measure the voltage across the resistor.

6. The system of claim 5, wherein the measurement device is powered inductively by a second conductor within the conduit system, the second conductor different from the first conductor.

7. The system of claim 6, wherein a clamp-on current transformer is coupled between the second conductor and the measurement device to inductively power the measurement device.

8. A method for determining ground impedance of a conduit system, the method comprising:
   accessing a first conductor housed within a conduit system;

wrapping a conductive tape a plurality of times about the first conductor to form a capacitive coupler such that capacitive coupling occurs between the conductive tape and the first conductor, the capacitive coupling operating to establish a voltage source;

coupling a resistor of known value between the capacitive coupler and a metal component of the conduit system; and measuring a voltage drop across the resistor, wherein the voltage drop is representative of the ground impedance of the conduit system.

9. The method of claim 8, wherein a voltage across the resistor of less than an ideal voltage, but greater than a zero voltage, indicates a weakening ground impedance of the conduit system.

10. The method of claim 9, further comprising providing an indication of the weakening ground impedance of the conduit system.

11. The method of claim 10, wherein the indication of the weakening ground impedance provides an alert to corrosion within the conduit system.

12. The method of claim 8, wherein the step of measuring is performed by a measurement device inductively powered by a second conductor housed within the conduit system, wherein the first conductor is different from the second conductor.

13. The method of claim 12, wherein a clamp-on current transformer is coupled between the second conductor and the measurement device to inductively power the measurement device.

14. The method of claim 8, wherein the conductor is an insulated conductor.

15. A method to determine the ground impedance of a conduit system, the method comprising:

calculating an impedance of the conduit system based on:
a voltage of a voltage source formed by a capacitive coupling between a first conductor and a coupler having a known impedance value;
a known resistance value of a resistor in communication between the voltage source and a metal component of the conduit system;
a voltage to ground value for the conduit system; and
a measured voltage drop across the resistor;

determining whether the impedance of the conduit system exceeds a failure threshold; and in response to determining that the impedance exceeds the failure threshold, generating a ground fault alert.

16. The method of claim 15, further comprising:

in response to determining that the impedance no longer exceeds the failure threshold, clearing the ground fault alert.

17. The method of claim 15, wherein the measured voltage drop across the resistor is measured by a measurement device inductively powered by a second conductor housed within the conduit system, wherein the first conductor is different from the second conductor.

18. The method of claim 15, wherein the coupler having the known impedance value is a conductive tape wrapped a plurality of times about the first conductor to form a conductive sheath.

* * * * *